(12) United States Patent
Schleicher et al.

(10) Patent No.: US 9,610,435 B2
(45) Date of Patent: Apr. 4, 2017

(54) ANCHORING UNITS FOR IMPLANTABLE ELECTRICAL STIMULATION SYSTEMS AND METHODS OF MAKING AND USING

(71) Applicant: BOSTON SCIENTIFIC NEUROMODULATION CORPORATION, Valencia, CA (US)

(72) Inventors: Brett Daniel Schleicher, New York, NY (US); Michael Joo, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/720,718

(22) Filed: May 22, 2015

(65) Prior Publication Data
US 2015/0250998 A1   Sep. 10, 2015

Related U.S. Application Data

(62) Division of application No. 12/755,756, filed on Apr. 7, 2010, now abandoned.
(Continued)

(51) Int. Cl.
*A61N 1/05* (2006.01)

(52) U.S. Cl.
CPC .............. *A61N 1/05* (2013.01); *A61N 1/0558* (2013.01); *A61N 1/057* (2013.01)

(58) Field of Classification Search
CPC ....... A61N 1/057; A61N 1/0573; A61N 1/059
(Continued)

(56) References Cited

U.S. PATENT DOCUMENTS 3,754,555 A   8/1973   Schmitt
3,814,104 A   6/1974   Irnich
(Continued)

FOREIGN PATENT DOCUMENTS

WO   2004028618       4/2004
WO   2005028023 A1   3/2005
(Continued)

OTHER PUBLICATIONS

Official Communication for U.S. Appl. No. 12/755,756 mailed Apr. 16, 2014.
(Continued)

*Primary Examiner* — Christopher A Flory
(74) *Attorney, Agent, or Firm* — Lowe Graham Jones PLLC; Bruce E. Black

(57) ABSTRACT

An anchoring unit for an implantable lead includes a body, a plurality of anchoring members, and at least one connecting element coupling together at least two of the anchoring members that are positioned adjacent to one another. The body is configured and arranged for positioning along a portion of an outer surface of a lead. The body has a first end, a second end, and a longitudinal axis extending therebetween. The first end is configured and arranged for placement on the lead so that the first end is positioned more distally on the lead than the second end. Each anchoring member has a proximal end and a distal end. The proximal end of each anchoring member extends from the body and the distal end of each anchoring member anchors to patient tissue upon implantation of the anchoring unit into the patient.

18 Claims, 11 Drawing Sheets

Related U.S. Application Data

(60) Provisional application No. 61/167,358, filed on Apr. 7, 2009.

(58) Field of Classification Search
USPC .......................................... 607/2, 116, 126
See application file for complete search history.

(56) References Cited

U.S. PATENT DOCUMENTS

| | | | |
|---|---|---|---|
| 4,112,952 A | 9/1978 | Thomas et al. | |
| 4,280,512 A | 7/1981 | Karr et al. | |
| 4,301,815 A * | 11/1981 | Doring | A61N 1/057 607/126 |
| 4,378,023 A | 3/1983 | Trabucco | |
| 4,706,682 A * | 11/1987 | Stypulkowski | A61B 5/042 600/379 |
| 4,796,643 A * | 1/1989 | Nakazawa | A61N 1/057 600/375 |
| 4,883,070 A * | 11/1989 | Hanson | A61N 1/057 607/116 |
| 4,913,147 A | 4/1990 | Fahlstrom et al. | |
| 4,989,617 A * | 2/1991 | Memberg | A61N 1/057 607/116 |
| 5,052,407 A | 10/1991 | Hauser et al. | |
| 5,314,462 A | 5/1994 | Heil, Jr. et al. | |
| 5,325,870 A | 7/1994 | Kroll et al. | |
| 5,466,255 A | 11/1995 | Franchi | |
| 5,492,119 A | 2/1996 | Abrams | |
| 5,507,802 A | 4/1996 | Imran | |
| 5,571,162 A | 11/1996 | Lin | |
| 5,609,623 A | 3/1997 | Lindegren | |
| 5,674,273 A | 10/1997 | Helland | |
| 5,868,741 A | 2/1999 | Chia et al. | |
| 5,871,532 A | 2/1999 | Schroeppel | |
| 5,922,014 A | 7/1999 | Warman et al. | |
| 5,948,014 A | 9/1999 | Valikai | |
| 5,957,966 A | 9/1999 | Schroeppel et al. | |
| 6,093,185 A | 7/2000 | Ellis et al. | |
| 6,181,969 B1 | 1/2001 | Gord | |
| 6,249,708 B1 | 6/2001 | Nelson et al. | |
| 6,345,198 B1 | 2/2002 | Mouchawar et al. | |
| 6,516,227 B1 | 2/2003 | Meadows | |
| 6,609,029 B1 | 8/2003 | Mann | |
| 6,609,032 B1 | 8/2003 | Woods | |
| 6,671,544 B2 | 12/2003 | Baudino | |
| 6,741,892 B1 | 5/2004 | Meadows | |
| 6,999,819 B2 * | 2/2006 | Swoyer | A61N 1/0558 607/117 |
| 7,130,700 B2 | 10/2006 | Gardeski et al. | |
| 7,187,983 B2 | 3/2007 | Dahlberg et al. | |
| 7,244,150 B1 | 7/2007 | Brase et al. | |
| 7,328,068 B2 * | 2/2008 | Spinelli | A61N 1/36007 607/39 |
| 7,343,202 B2 * | 3/2008 | Mrva | A61N 1/0524 607/116 |
| 7,369,894 B2 * | 5/2008 | Gerber | A61N 1/36071 607/133 |
| 7,437,193 B2 | 10/2008 | Parramon | |
| 7,463,934 B2 * | 12/2008 | Tronnes | A61N 1/05 607/133 |
| 7,565,198 B2 * | 7/2009 | Bennett | A61N 1/08 607/40 |
| 7,672,734 B2 | 3/2010 | Anderson et al. | |
| 7,761,165 B1 | 7/2010 | He et al. | |
| 7,835,801 B1 | 11/2010 | Sundararajan et al. | |
| 7,881,783 B2 * | 2/2011 | Bonde | A61N 1/0558 607/2 |
| 7,899,550 B1 | 3/2011 | Doan et al. | |
| 7,927,282 B2 | 4/2011 | Hettrick et al. | |
| 8,096,959 B2 | 1/2012 | Stewart et al. | |
| 8,452,420 B2 | 5/2013 | Flach et al. | |
| 8,469,954 B2 | 6/2013 | Young et al. | |
| 8,532,789 B2 | 9/2013 | Smits | |
| 9,107,750 B2 * | 8/2015 | Cartledge | A61B 17/068 |
| 2002/0111620 A1 * | 8/2002 | Cooper | A61B 8/12 606/41 |
| 2002/0151867 A1 | 10/2002 | McGuckin, Jr. et al. | |
| 2002/0156058 A1 | 10/2002 | Borkan | |
| 2003/0018358 A1 * | 1/2003 | Saadat | A61B 17/0401 606/232 |
| 2003/0078671 A1 * | 4/2003 | Lesniak | A61B 17/00234 623/23.64 |
| 2003/0093104 A1 * | 5/2003 | Bonner | A61B 17/3478 606/185 |
| 2003/0114905 A1 * | 6/2003 | Kuzma | A61N 1/0551 607/116 |
| 2003/0195600 A1 * | 10/2003 | Tronnes | A61N 1/05 607/116 |
| 2004/0116939 A1 * | 6/2004 | Goode | A61N 1/056 606/108 |
| 2004/0116992 A1 | 6/2004 | Wardle et al. | |
| 2004/0230279 A1 | 11/2004 | Cates et al. | |
| 2005/0080402 A1 * | 4/2005 | Santamore | A61B 17/00234 606/1 |
| 2005/0096720 A1 * | 5/2005 | Sharma | A61B 5/042 607/122 |
| 2005/0165465 A1 | 7/2005 | Pianca et al. | |
| 2005/0288722 A1 * | 12/2005 | Eigler | A61B 5/0215 607/9 |
| 2006/0004421 A1 * | 1/2006 | Bennett | A61N 1/08 607/41 |
| 2006/0095059 A1 * | 5/2006 | Bleich | A61B 17/1659 606/170 |
| 2006/0276871 A1 * | 12/2006 | Lamson | A61F 2/82 623/1.11 |
| 2007/0043414 A1 | 2/2007 | Fifer et al. | |
| 2007/0049980 A1 | 3/2007 | Zielinski et al. | |
| 2007/0080188 A1 * | 4/2007 | Spence | A61B 17/0401 227/175.1 |
| 2007/0123922 A1 * | 5/2007 | Cooper | A61B 8/12 606/191 |
| 2007/0150036 A1 | 6/2007 | Anderson | |
| 2007/0219595 A1 | 9/2007 | He | |
| 2007/0239243 A1 | 10/2007 | Moffitt et al. | |
| 2007/0293923 A1 | 12/2007 | Soltis et al. | |
| 2007/0299481 A1 * | 12/2007 | Syed | A61N 1/0558 607/40 |
| 2008/0039889 A1 * | 2/2008 | Lamson | A61B 17/0401 606/194 |
| 2008/0071320 A1 | 3/2008 | Brase | |
| 2008/0103569 A1 | 5/2008 | Gerber | |
| 2008/0103572 A1 * | 5/2008 | Gerber | A61N 1/0529 607/116 |
| 2008/0183253 A1 * | 7/2008 | Bly | A61N 1/0558 607/116 |
| 2008/0183266 A1 | 7/2008 | D'Aquanni et al. | |
| 2008/0208247 A1 * | 8/2008 | Rutten | A61M 25/04 606/205 |
| 2008/0208248 A1 * | 8/2008 | Rutten | A61M 25/04 606/205 |
| 2008/0208303 A1 * | 8/2008 | Rutten | A61M 25/04 607/116 |
| 2008/0208339 A1 * | 8/2008 | Rutten | A61M 25/04 623/11.11 |
| 2009/0018523 A1 * | 1/2009 | Lamson | A61F 2/82 604/506 |
| 2009/0054949 A1 * | 2/2009 | Alexander | A61N 1/05 607/37 |
| 2009/0192439 A1 * | 7/2009 | Lamson | A61B 17/0401 604/22 |
| 2009/0204128 A1 * | 8/2009 | Lamson | A61B 17/0401 606/151 |
| 2009/0248095 A1 * | 10/2009 | Schleicher | A61N 1/0558 607/2 |
| 2009/0254151 A1 * | 10/2009 | Anderson | A61N 1/05 607/59 |
| 2010/0163054 A1 * | 7/2010 | Breznel | A61B 17/12022 128/831 |

(56) References Cited

U.S. PATENT DOCUMENTS

| | | |
|---|---|---|
| 2010/0168806 A1* | 7/2010 | Norlin-Weissenrieder ........ A61N 1/056 607/3 |
| 2010/0256696 A1 | 10/2010 | Schleicher et al. |
| 2011/0071591 A1* | 3/2011 | Bolea .................... A61N 1/0556 607/42 |
| 2011/0125163 A1* | 5/2011 | Rutten .................... A61M 25/04 606/108 |
| 2011/0166649 A1* | 7/2011 | Gross .................... A61F 2/2445 623/2.36 |
| 2011/0208295 A1* | 8/2011 | Cartledge ............ A61B 17/068 623/2.11 |
| 2011/0251662 A1 | 10/2011 | Griswald et al. |
| 2012/0010681 A1* | 1/2012 | Bolea .................... A61N 1/0556 607/42 |
| 2012/0053665 A1 | 3/2012 | Stolz et al. |
| 2012/0165855 A1* | 6/2012 | Shalon .................... A61F 5/0036 606/191 |
| 2012/0184809 A1* | 7/2012 | Bleich ................ A61B 17/1659 600/104 |
| 2012/0232459 A1* | 9/2012 | Dann ................ A61B 17/00234 604/8 |
| 2012/0323253 A1 | 12/2012 | Garai et al. |
| 2013/0066411 A1 | 3/2013 | Thacker et al. |
| 2013/0317414 A1* | 11/2013 | Shalon .................... A61F 5/0079 604/9 |
| 2014/0031909 A1* | 1/2014 | Ye ........................ A61N 1/0558 607/117 |
| 2014/0330287 A1 | 11/2014 | Thompson-Nauman et al. |
| 2014/0343645 A1 | 11/2014 | Wechter |
| 2014/0343656 A1 | 11/2014 | Wechter |
| 2015/0039069 A1 | 2/2015 | Rys et al. |
| 2015/0051616 A1 | 2/2015 | Haasl et al. |
| 2015/0081014 A1* | 3/2015 | Gross .................... A61F 2/2445 623/2.37 |

FOREIGN PATENT DOCUMENTS

| | | |
|---|---|---|
| WO | 2013082283 | 6/2013 |
| WO | 2015167800 | 11/2015 |

OTHER PUBLICATIONS

Official Communication for U.S. Appl. No. 12/755,756 mailed Nov. 27, 2013.
Official Communication for U.S. Appl. No. 12/755,756 mailed Jul. 22, 2013.
Official Communication for U.S. Appl. No. 12/755,756 mailed Mar. 28, 2013.
Official Communication for U.S. Appl. No. 12/755,756 mailed Aug. 16, 2012.
Official Communication for U.S. Appl. No. 12/755,756 mailed Apr. 11, 2012.
Official Communication for U.S. Appl. No. 12/755,756 mailed Dec. 4, 2014.
Official Communication for U.S. Appl. No. 12/755,756 mailed Feb. 25, 2015.
U.S. Appl. No. 14/634,253, filed Feb. 27, 2015.
U.S. Appl. No. 14/690,071, filed Apr. 17, 2015.
U.S. Appl. No. 62/111,596, filed Feb. 3, 2015.
U.S. Appl. No. 62/006,824, filed Jun. 2, 2014.

* cited by examiner

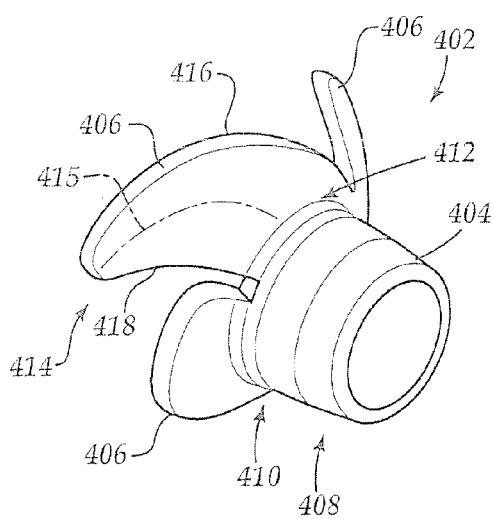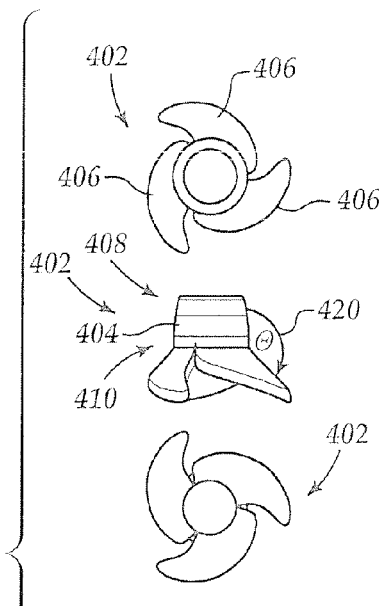
Fig.4A  Fig.4B
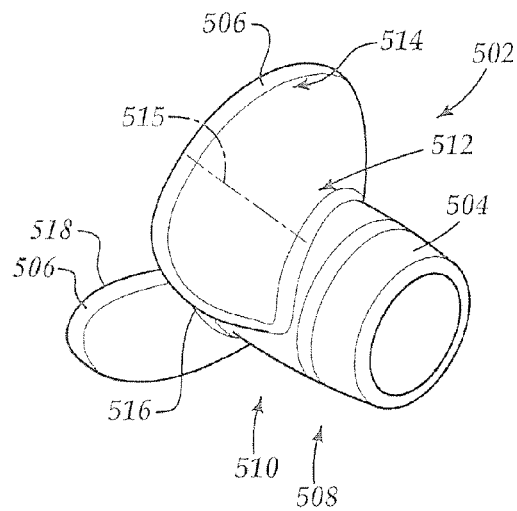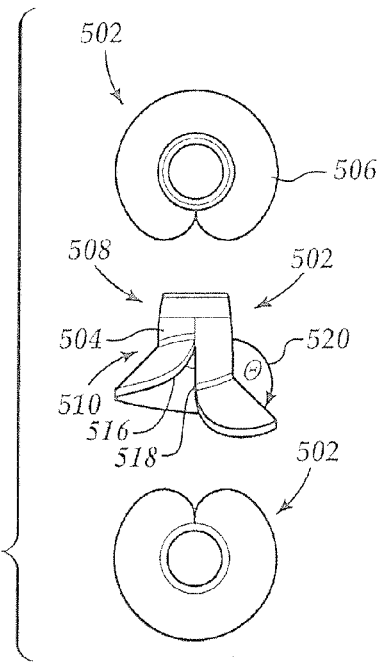
Fig.5A  Fig.5B

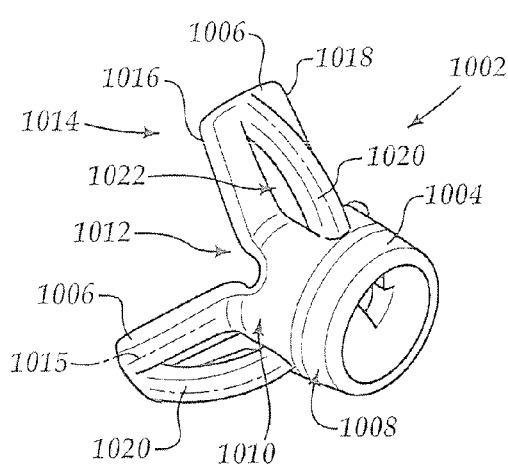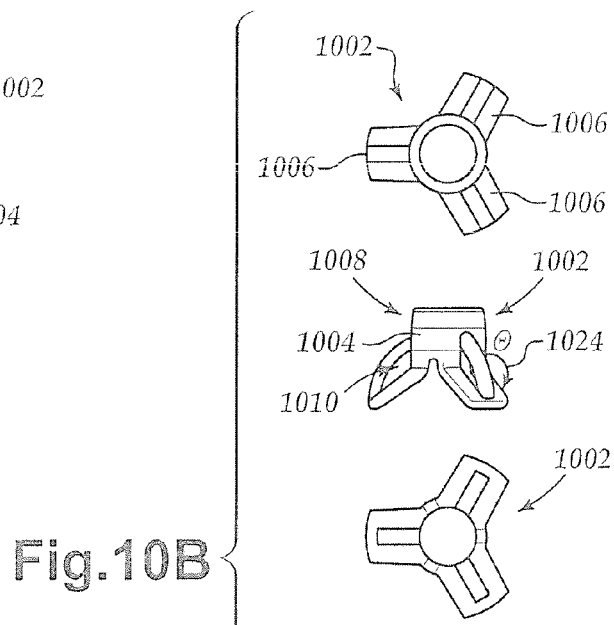
Fig.10A  Fig.10B
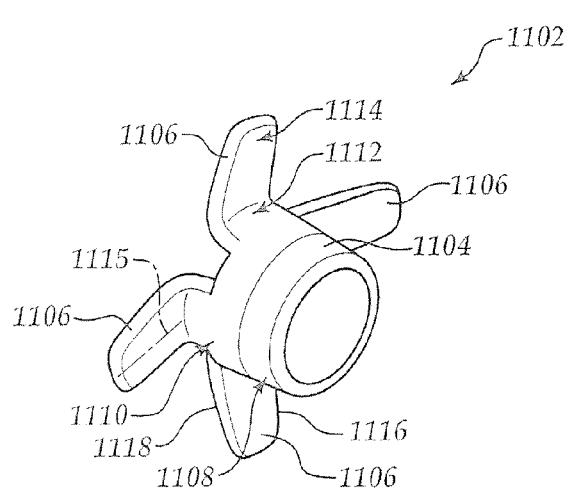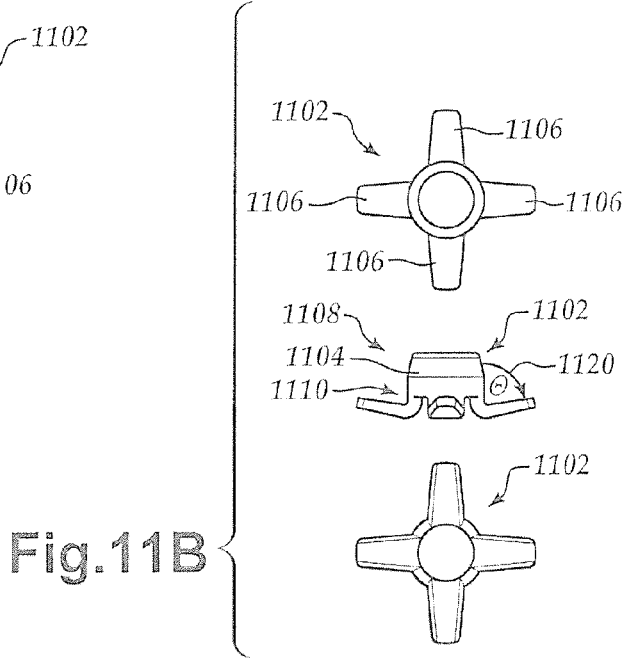
Fig.11A  Fig.11B

ANCHORING UNITS FOR IMPLANTABLE ELECTRICAL STIMULATION SYSTEMS AND METHODS OF MAKING AND USING

CROSS REFERENCE TO RELATED APPLICATIONS

This application is a divisional of U.S. patent application Ser. No. 12/755,756 filed Apr. 7, 2010 which claims the benefit under 35 U.S.C. §119(e) of U.S. Provisional Patent Application Ser. No. 61/167,358 filed on Apr. 7, 2009, both of which are incorporated herein by reference.

FIELD

The present invention is directed to the area of implantable electrical stimulation systems and methods of making and using the systems. The present invention is also directed to implantable electrical stimulation leads having one or more anchoring units coupled to the lead to facilitate fixing of the lead within patient tissue, as well as methods of making and using the leads, anchoring units, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In at least one embodiment, an anchoring unit for an implantable lead includes a body, a plurality of anchoring members, and at least one connecting element coupling together at least two of the anchoring members that are positioned adjacent to one another. The body is configured and arranged for positioning along a portion of an outer surface of a lead. The body has a first end, a second end, and a longitudinal axis extending therebetween. The first end is configured and arranged for placement on the lead so that the first end is positioned more distally on the lead than the second end. Each anchoring member has a proximal end and a distal end. The proximal end of each anchoring member extends from the body and the distal end of each anchoring member anchors to patient tissue upon implantation of the anchoring unit into the patient.

In another embodiment, an anchoring unit for an implantable lead includes a body, at least one anchoring member, and at least one leaf spring. The body is configured and arranged for positioning along a portion of an outer surface of the lead. The at least one anchoring member has a proximal end and a distal end. The proximal end extends from the body and the distal end is configured and arranged for anchoring the anchoring unit to tissue of a patient upon implantation of the anchoring unit into the patient. The at least one leaf spring has a first end and a second end. The first end is coupled to the body and the second end is coupled to the distal end of the at least one anchoring member.

In yet another embodiment, an anchoring unit for an implantable lead includes a body and at least one anchoring member. The body is configured and arranged for positioning along a portion of an outer surface of a lead. The body has a first end and a second end and a longitudinal axis extending between the first end and the second end. The first end is configured and arranged for placement on the lead so that the first end is positioned more distally on the lead than the second end. The at least one anchoring member has a proximal end and a distal end. The proximal end extends from the body and the distal end is configured and arranged for anchoring the anchoring unit to tissue of a patient upon implantation into the patient. At least a portion of one anchoring member extends in a direction that forms an angle with the longitudinal axis of the body distal to the at least one anchoring member that is no greater than ninety degrees.

In another embodiment, an anchoring unit for an implantable lead includes a body and at least one anchoring member. The body is configured and arranged for positioning along a portion of an outer surface of the lead. The at least one anchoring member has a proximal end, a distal end, and a longitudinal axis. The proximal end of the at least one anchoring member extends from the body and the distal end of the at least one anchoring member is configured and arranged for anchoring the anchoring unit to tissue of a patient upon implantation into the patient. The at least one anchoring member extends from the body such that the at least one anchoring unit is arranged in a helical or spiral arrangement.

In yet another embodiment, an anchoring unit for an implantable lead includes a body and at least one anchoring member. The body is configured and arranged for positioning along a portion of an outer surface of the lead. The at least one anchoring member has a proximal end, a distal end, and a longitudinal axis. The proximal end of the at least one anchoring member extends from the body and the distal end of the at least one anchoring member is configured and arranged for anchoring the anchoring unit to tissue of a patient upon implantation into the patient. The distal end of the at least one anchoring member is wider than the proximal end of the at least one anchoring unit.

In another embodiment, an anchoring unit for an implantable lead includes a body and a single anchoring member. The body is configured and arranged for positioning along a portion of an outer surface of the lead. The single anchoring member has a proximal end, a distal end, and a longitudinal axis. The proximal end of the single anchoring member extends from the body and the distal end of the single anchoring member is configured and arranged for anchoring the anchoring unit to tissue of a patient upon implantation into the patient. The single anchoring member extends from the body in a helical arrangement that extends at least one revolution around a circumference of the body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic perspective view of a first embodiment of an anchoring unit for an electrical stimulation system, the anchoring unit including a body and anchoring members with an arcing longitudinal axis, according to the invention;

FIG. 4B is a schematic bottom view, side view, and top view of the anchoring unit shown in FIG. 4A, according to the invention;

FIG. 5A is a schematic perspective view of a second embodiment of an anchoring unit for an electrical stimulation system, the anchoring unit including a body and anchoring members coupled to the body in a helical arrangement, according to the invention;

FIG. 5B is a schematic bottom view, side view, and top view of the anchoring unit shown in FIG. 5A, according to the invention;

FIG. 10A is a schematic perspective view of an eighth embodiment of an anchoring unit for an electrical stimulation system, the anchoring unit including a body and anchoring members coupled to the body, each anchoring member having a distal end that also couples to the body via a leaf spring, according to the invention;

FIG. 10B is a schematic bottom view, side view, and top view of the anchoring unit shown in FIG. 10A, according to the invention;

FIG. 11A is a schematic perspective view of a ninth embodiment of an anchoring unit for an electrical stimulation system, the anchoring unit including a body and distally-biased anchoring members, according to the invention;

FIG. 11B is a schematic bottom view, side view, and top view of the anchoring unit shown in FIG. 11A, according to the invention;

DETAILED DESCRIPTION

The present invention is directed to the area of implantable electrical stimulation systems and methods of making and using the systems. The present invention is also directed to implantable electrical stimulation leads having one or more anchoring units coupled to the lead to facilitate fixing of the lead within patient tissue, as well as methods of making and using the leads, anchoring units, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291;

11/327,880; 11/375,638; 11/393,991; and 11/396,309, all of which are incorporated by reference.

Figure 1:
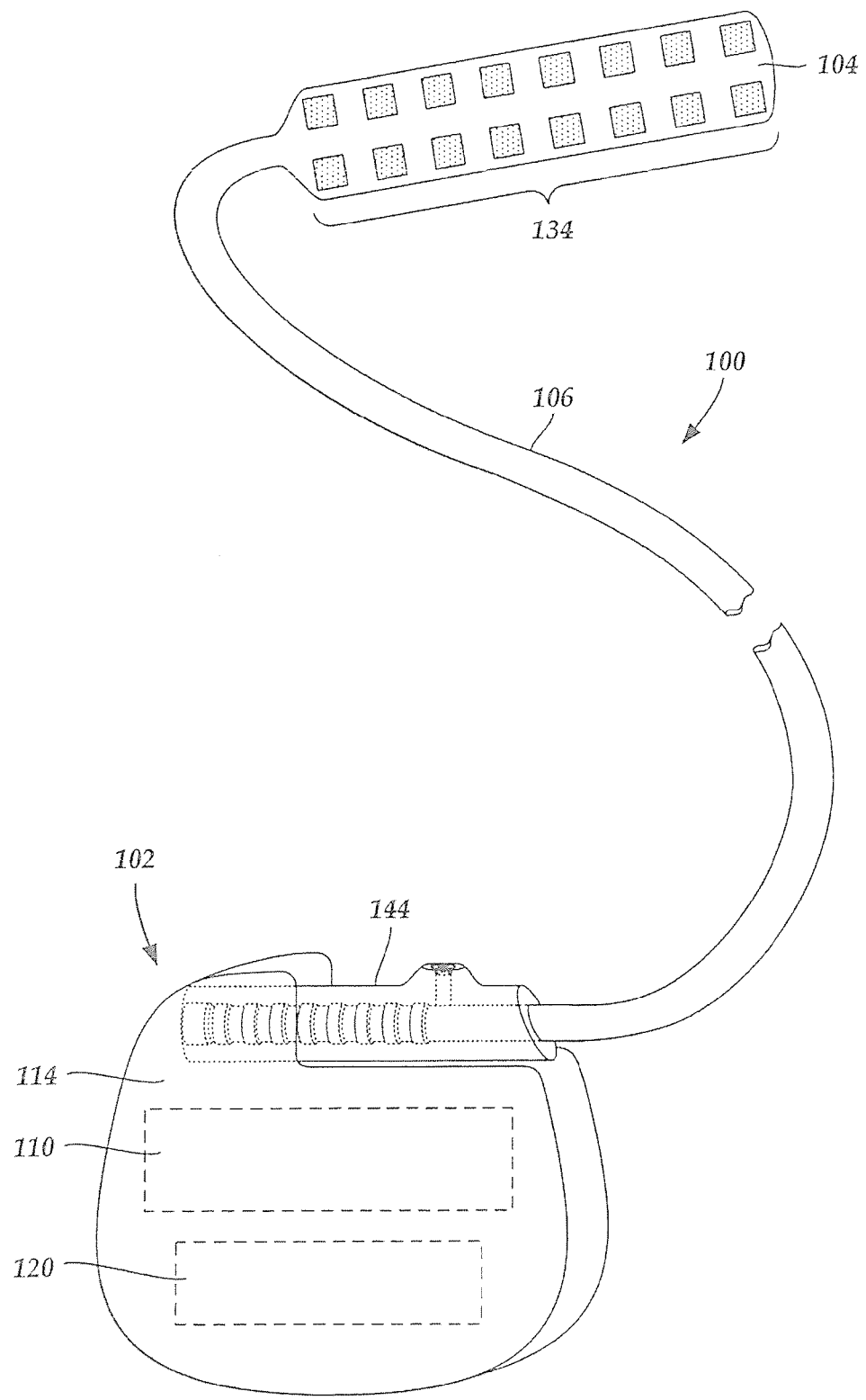
FIG. 1 is a schematic view of one embodiment of an electrical stimulation system, according to the invention.
Figure 2:
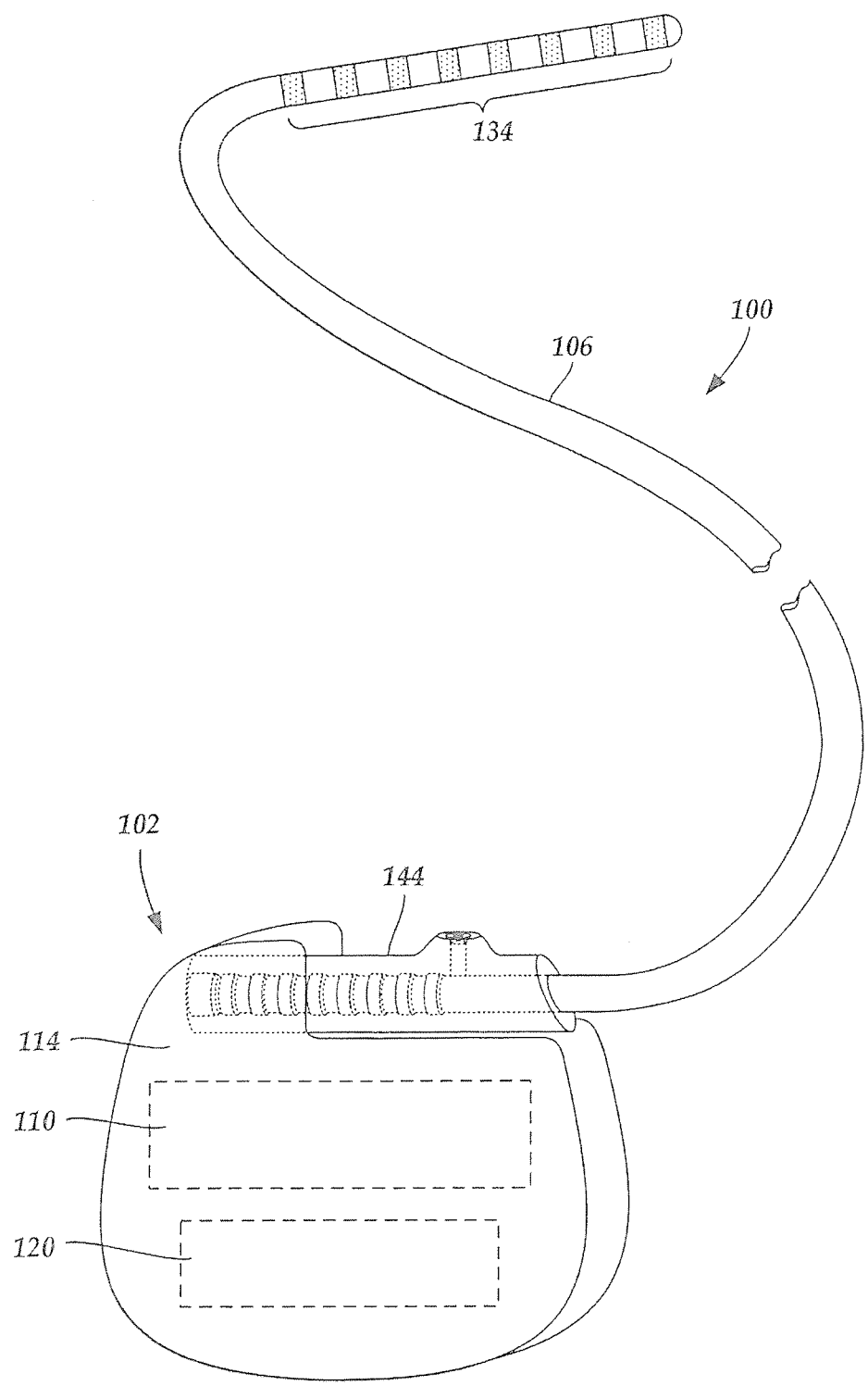
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, well combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
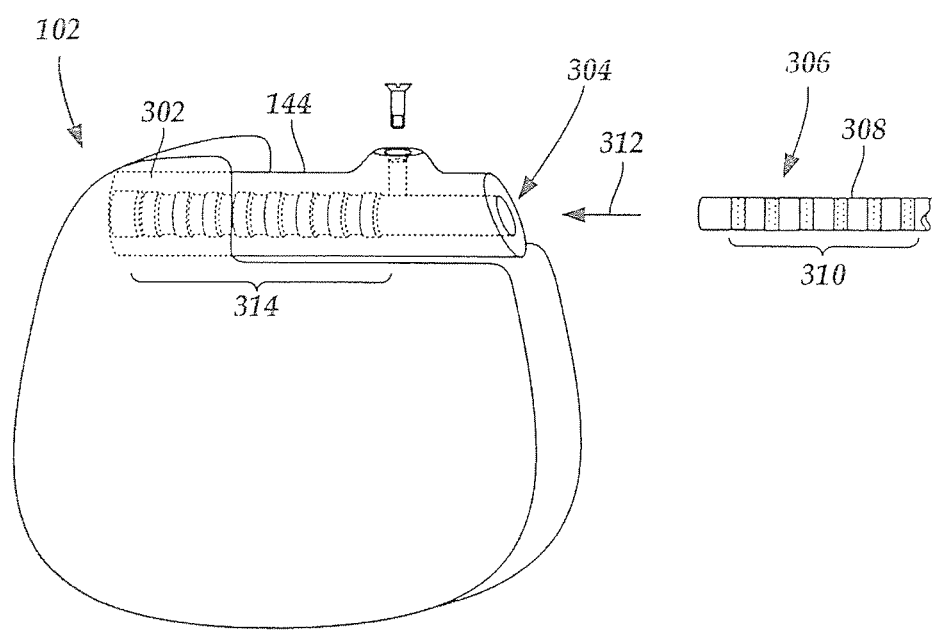
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
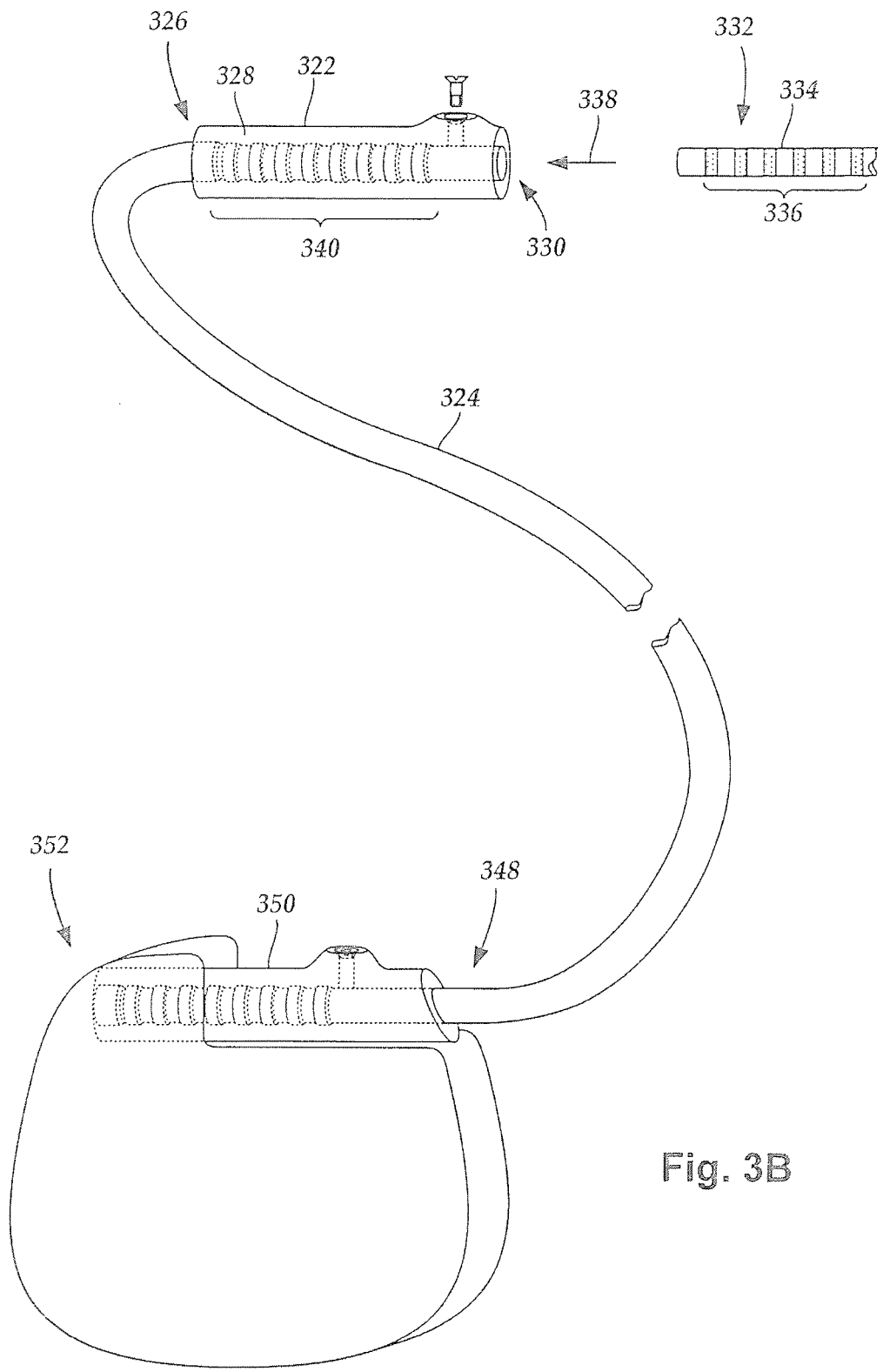
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

Electrode placement can be important for obtaining efficacious patient response to stimulation. Sometimes a distal end of a lead may migrate from an intended treatment site over time due to patient movement. When a distal end of a lead migrates far enough away from the intended treatment site, a loss of efficacy may occur and surgical re-implantation may become necessary to re-establish efficacy.

One way to reduce migration of the distal end of an implanted lead is to anchor the distal end of the lead within patient tissue. In at least some embodiments, anchoring units are described for use with implantable electrical stimulation systems. In at least some embodiments, one or more anchoring units may be disposed along a longitudinal axis of the lead body (see e.g., FIGS. 13 and 14). One or more anchoring units may be positioned on the lead body distal to the electrodes, in-between two or more electrodes, proximal to the electrodes, or any combination thereof. The anchoring units may be different sizes and shapes. When multiple anchoring units are disposed on a lead body, the anchoring units may either be all of similar size and shape, or one or more of the anchoring units may have different sizes or shapes from other anchoring units disposed on the lead body. Furthermore, adjacent anchoring units disposed on the lead body may be evenly-spaced, or irregularly spaced from one another. In at least some embodiments, the shapes, sizes, or arrangements of anchoring units disposed on a lead body may be selected based, at least in part, on a specific indication or a specific anatomical location.

The anchoring units may be formed from any suitable biocompatible material including, for example, polyurethane, silicone rubber, polytetrafluoroethylene, polyethylene, nylon, metal, nitinol, and the like or combinations thereof. In at least some embodiments, at least a portion of the anchoring units are formed integrally with the lead body (e.g., by overmolding a body of an anchoring unit to the lead body, reflowing a body of an anchoring unit to the lead body, or the like). In at least some other embodiments, anchoring units may be coupled to the lead body at selected locations along a longitudinal axis of the lead using any suitable bonding process including, for example, chemical bonding, welding, interference fit, and the like or combinations thereof.

FIG. 4A is a schematic perspective view of a first embodiment of an anchoring unit 402 for an electrical stimulation system. The anchoring unit 402 includes a body 404 and one or more anchoring members 406. The body 404 includes a first end 408 and a second end 410 and is configured and arranged to be disposed over at least a portion of an outer surface of the lead body (see e.g., FIGS. 13 and 14). In at least some embodiments, the first end 408 is positioned more distally than the second end 410 when the anchoring unit 402 is disposed on the lead body (106 in FIG. 1). The anchoring members 406 each include a proximal end 412, a distal end 414, and a longitudinal axis 415 defined by a first side 416 and a second side 418.

In some embodiments, the anchoring members form a spiral arrangement. In FIG. 4A, the first sides 416 of the anchoring members 406 are arcing leading edges and the second sides 418 are lagging edges, thereby forming an arcing longitudinal axis 415. In at least some embodiments, the lagging second sides 418 are also arcing. In at least some embodiments, the first sides 416 of the anchoring members 406 are similarly-arced to form a spiral pattern. In at least some embodiments, the first sides 416 of the anchoring members 406 are longer in length than the second sides 418 of the anchoring members 406. In at least some embodiments, the first side 416 and the second side 418 of the anchoring members 402 taper inward such that the proximal ends 412 are wider than the distal ends 414.

In at least some embodiments, the distal end 414 of at least one of the anchoring members 406 tapers to form a point. In a preferred embodiment, the point is rounded. It may be an advantage to employ one or more anchoring units 402 with anchoring members 406 that taper to points because a medical practitioner may be able to rotate the lead to further engage the anchor members 406 within patient tissue during implantation, thereby increasing the anchoring ability of the lead.

FIG. 4B is a schematic bottom view, side view, and top view of the anchoring unit 402. In at least some embodiments, the anchoring members 406 extend from the second end 410 of the body 404 along a common transverse axis of the body 404. In at least some embodiments, the anchoring members 406 are proximally biased. In other words, when the anchoring unit 402 is disposed on the lead body (106 in FIG. 1) so that the first end 408 is more distal on the lead body (106 in FIG. 1) than the second end 410, the anchoring members 406 form an angle with the longitudinal axis of the body 404 that is at least ninety degrees, as shown by angle Θ 420.

In some embodiments, the anchoring unit includes a single anchoring member that extends from the body in a helical arrangement. FIG. 5A is a schematic perspective view of a second embodiment of an anchoring unit 502. The anchoring unit 502 includes a body 504 and one anchoring member 506. The body 504 includes a first end 508 and a second end 510 and the anchoring member 506 includes a proximal end 512, a distal end 514, a longitudinal axis 515, a first side 516, and a second side 518.

In at least some embodiments, the proximal end 512 of the anchoring member 506 extends at least three-fourths of one complete revolution around a circumference of the body 504. In at least some embodiments, the proximal end 512 of the anchoring member 506 extends at least one complete revolution around the circumference of the body 504. In at least some embodiments, the proximal end 512 of the anchoring member 506 couples to the body 504 in a helical arrangement along a longitudinal axis of the body 504 such that the first side 516 and the second side 518 of the anchoring member 506 couple to the body 504 along different transverse points along the longitudinal axis of the body 504. In at least some embodiments, the pitch and the number of revolutions of the anchoring member 506 around a circumference of the body 504 may be tailored to the specific indication or the specific anatomical location of the implantation of the lead body (106 in FIG. 1) to which one or more of the anchoring units 502 may be coupled.

In at least some embodiments, the first side 516 and the second side 518 of the anchoring member 502 taper outward such that the distal end 514 is wider than the proximal end 512. In at least some embodiments, the first side 516 and the second side 518 of the anchoring member 502 taper inward such that the proximal end 512 is wider than the distal end 514. In at least some embodiments, the proximal end 512 and the distal end 514 are of approximately equal width.

FIG. 5B is a schematic bottom view, side view, and top view of the anchoring unit 502. In at least some embodiments, the anchoring member 506 is proximally biased. In other words, when the anchoring unit 502 is disposed on the lead body (106 in FIG. 1) so that the first end 508 is more distal on the lead body (106 in FIG. 1) than the second end 510, the anchoring member 506 forms an angle with the longitudinal axis of the body 504 that is at least ninety degrees, as shown by angle Θ 520.

Figure 6A:
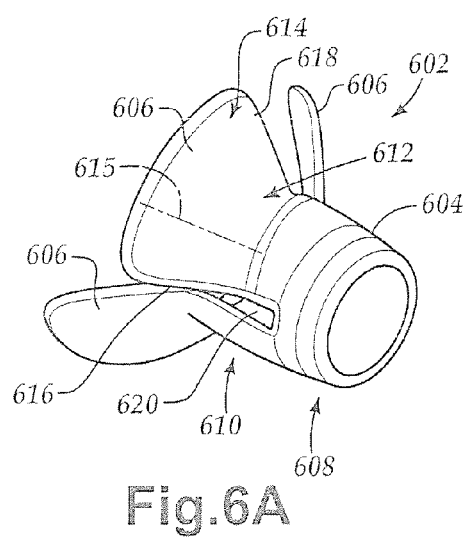
FIG. 6A is a schematic perspective view of a third embodiment of an anchoring unit for an electrical stimulation system, the anchoring unit including a body defining at least one slit and anchoring members coupled to the body in a helical arrangement, according to the invention.

In some embodiments, the body includes one or more tapered anchoring members. FIG. 6A is a schematic perspective view of a third embodiment of an anchoring unit 602. The anchoring unit 602 includes a body 604 and at least one anchoring member 606. The body 604 includes a first end 608 and a second end 610. The anchoring member 606 includes a proximal end 612, a distal end 614, a longitudinal axis 615, a first side 616, and a second side 618. The body 604 also defines one or more slits 620 along at least portion of the second end 610 of the body 604 between adjacent anchoring members 606. In at least some embodiments, the one or more slits 616 extend in a direction that is parallel to a longitudinal axis of the body 604. In at least some embodiments, the one or more slits 616 facilitate the anchoring members 606 lying flat (e.g., during insertion of the lead into a patient).

In at least some embodiments, the first side 616 and the second side 618 of the anchoring member 602 taper outward such that the distal end 614 is wider than the proximal end 612. In at least some embodiments, the proximal ends 612 of two or more anchoring members 606 extend from the body 604 in a helical pattern along a longitudinal axis of the body 604 such that the first side 616 and the second side 618 of each of two or more the anchoring units 602 extend from the body 604 along different transverse axes of the body 604. In at least some embodiments, the pitch and the number of revolutions of the anchoring members 606 around a circumference of the body 604 may be tailored to the specific indication or the specific anatomical location of the implantation of the lead body (106 in FIG. 1) to which one or more of the anchoring units 602 may be coupled.

Figure 6B:
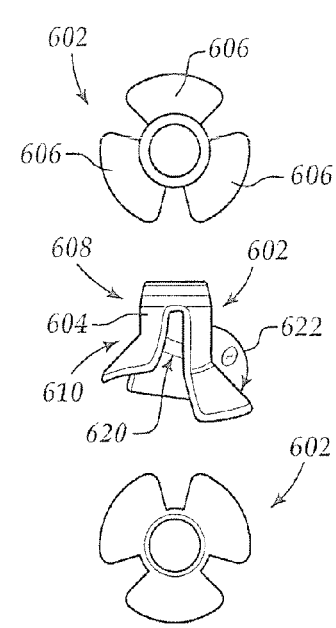
FIG. 6B is a schematic bottom view, side view, and top view of the anchoring unit shown in FIG. 6A, according to the invention.

FIG. 6B is a schematic bottom view, side view, and top view of the anchoring unit 602. In at least some embodiments, the anchoring members 606 are proximally biased. In other words, when the anchoring unit 602 is disposed on the lead body (106 in FIG. 1) so that the first end 608 is more distal on the lead body (106 in FIG. 1) than the second end 610, the anchoring members 606 form an angle with the longitudinal axis of the body 604 that is at least ninety degrees, as shown by angle Θ 622.

Figure 7A:
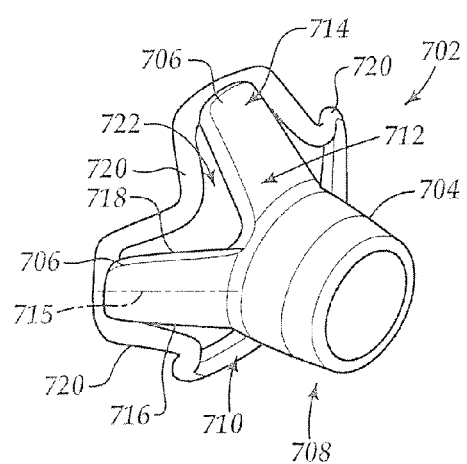
FIG. 7A is a schematic perspective view of a fourth embodiment of an anchoring unit for an electrical stimulation system, the anchoring unit including a body, anchoring members coupled to the body, and connecting elements coupling distal ends of the anchoring members to one another, according to the invention.

In some embodiments, one or more connecting elements couple to adjacent anchoring members. FIG. 7A is a schematic perspective view of a fourth embodiment of an anchoring unit 702. The anchoring unit 702 includes a body 704 and at least one anchoring member 706. The body 704 includes a first end 708 and a second end 710. The anchoring unit 702 includes a body 704 and at least one anchoring member 706. The body 704 includes a first end 708 and a second end 710. The anchoring member 706 includes a proximal end 712, a distal end 714, a longitudinal axis 715, a first side 716, and a second side 718.

In at least some embodiments, the first side 716 and the second side 718 of the anchoring member 706 taper such that the proximal end 712 of the anchoring member 706 is wider than the distal end 714. In at least some embodiments, the distal end 714 of at least one of the anchoring members 706 tapers to form a point. In a preferred embodiment, the point is rounded.

In at least some embodiments, two or more of the anchoring members 706 may be coupled to one another by a connecting element 720. For example, two adjacent anchoring members 706 may be coupled to one another by one or more connecting elements 720. In at least some embodiments, the distal end 714 of each anchoring member 706 is coupled to the distal end 714 of each adjacent anchoring member 706 by connecting elements 720. In at least some embodiments, a single connecting element 720 connects adjacent distal ends 714 to one another. In at least some embodiments, a plurality of connecting elements 720 connect adjacent distal ends 714 to one another. In at least some other embodiments, a single connecting element 720 connects each of the adjacent distal ends 714 together. In at least some embodiments, an open space 722 is formed between the connecting element 720 and adjacent anchoring members 706.

It will be understood that the one or more connecting elements 720 may couple adjacent anchoring members 706 at locations along the longitudinal axis of the anchoring members 706 other than the distal ends 714. For example, the connecting element may couple to a given anchoring member 706 at a position between the proximal end 712 and a distal end 714 of the anchoring member 706. In at least some embodiments, the connecting members 720 are formed with the anchoring unit 702. In at least some other embodiments, the connecting members 720 are formed subsequently assembled.

Additionally, in at least some embodiments, the connecting elements 702 are configured and arranged to fold flat against the lead body (106 in FIG. 1). For example, in at least some embodiments, the connecting elements 720 are configured and arranged to fold into open spaces between the anchoring members 706 when the anchoring members 706 are folded against the lead body (106 in FIG. 1). In at least some embodiments, at least one of the connecting elements 702 includes at least one bend to facilitate folding flat. In at least some embodiments, at least one of the connecting elements 702 is articulated to facilitate folding flat. In at least some embodiments, the connecting elements 720 increase the anchoring ability of the anchoring unit 702 by further facilitating tissue ingrowth.

Figure 7B:
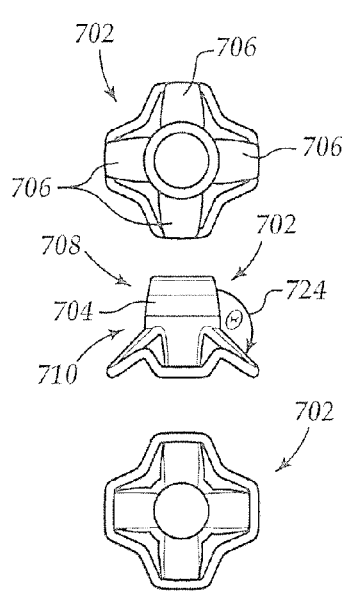
FIG. 7B is a schematic bottom view, side view, and top view of the anchoring unit shown in FIG. 7A, according to the invention.

FIG. 7B is a schematic bottom view, side view, and top view of the anchoring unit 702. In at least some embodiments, the anchoring members 706 extend from the second end 710 of the body 704 along a common transverse axis of the body 704. In at least some embodiments, the anchoring members 706 are proximally biased. In other words, when the anchoring unit 702 is disposed on the lead body (106 in FIG. 1) so that the first end 708 is more distal on the lead body (106 in FIG. 1) than the second end 710, the anchoring members 706 form an angle with the longitudinal axis of the body 704 that is at least ninety degrees, as shown by angle Θ 724.

Figure 8A:
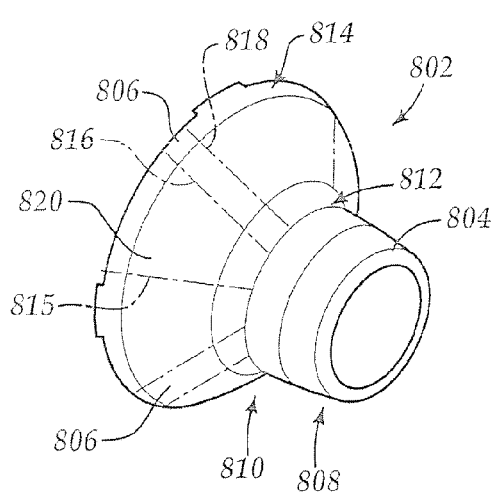
FIG. 8A is a schematic perspective view of a fifth and a sixth embodiment of an anchoring unit for an electrical stimulation system, the anchoring unit including a body and at least one anchoring member, according to the invention.

In at least some embodiments, the connective element may include a membrane coupling at least two adjacent anchoring members to one another. FIG. 8A is a schematic perspective view of a fifth embodiment of an anchoring unit 802. The anchoring unit 802 includes a body 804 and at least one anchoring member 806. The body 804 includes a first end 808 and a second end 810. The anchoring unit 802 includes a body 804 and at least one anchoring member 806. The body 804 includes a first end 808 and a second end 810. The anchoring member 806 includes a proximal end 812, a distal end 814, a longitudinal axis 815, a first side 816, and a second side 818.

In at least some embodiments, the first side 816 and the second side 818 of the anchoring member 806 taper such that the proximal end 812 of the anchoring member 806 is wider than the distal end 814. In at least some embodiments, the distal end 814 of at least one of the anchoring members 806 tapers to form a point. In a preferred embodiment, the point is rounded. In at least some embodiments, the first side 816 and the second side 818 of the anchoring member 806 taper such that the distal end 814 of the anchoring member 806 is wider than the proximal end 812. In at least some embodiments, the first side 816 and the second side 818 of the anchoring member 806 are of approximately equal width.

In at least some embodiments, two or more of the anchoring members 806 may be coupled to one another by a connecting element 820. In some embodiments, the connecting element 820 comprises a membrane, or sheath, that couples two or more of the anchoring members 806 to one another. In at least some embodiments, the connective element 820 has a thickness that is substantially thinner than the anchoring members 806. In at least some embodiments, the connecting element 820 forms a complete revolution around the body 804. In at least some embodiments, the connective element 820 covers at least a portion of at least one of the anchoring members 806. In at least some embodiments, the connecting element 820 substantially entirely covers each of the anchoring members 806. In at least some embodiments, the connecting element 820 completely covers each of the anchoring members 806. In at least some embodiments, at least a portion of at least one of the anchoring members 806 may need to deform onto itself while in a folded position (e.g., during insertion of the lead into a patient).

Figure 8B:
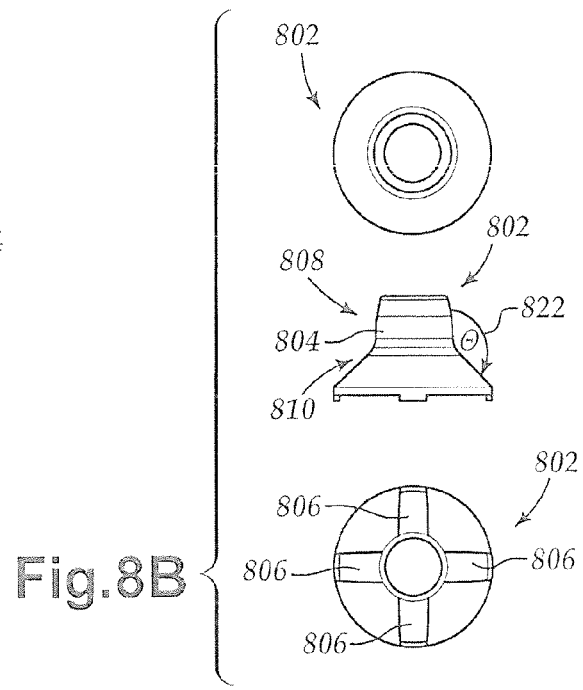
FIG. 8B is a schematic bottom view, side view, and top view of the anchoring unit shown in FIG. 8A, according to the invention.

FIG. 8B is a schematic bottom view, side view, and top view of the anchoring unit 802. In at least some embodiments, the anchoring members 806 extend from the second end 810 of the body 804 along a common transverse axis of the body 804. In at least some embodiments, the anchoring members 806 are proximally biased. In other words, when the anchoring unit 802 is disposed on the lead body (106 in FIG. 1) so that the first end 808 is more distal on the lead body (106 in FIG. 1) than the second end 810, the anchoring members 806 form an angle with the longitudinal axis of the body 804 that is at least ninety degrees, as shown by angle Θ 822.

In a sixth embodiment of the anchoring unit, also shown by FIGS. 8A and 8B, the anchoring unit 802 includes a single anchoring member 806 that extends around the entire circumference of the body 804. In some embodiments, the anchoring member 806 is a constant thickness. In at least some other embodiments, the thickness of the anchoring member 806 may vary. In at least some embodiments, the anchoring member 806 may define one or more cutouts for promoting tissue ingrowth.

Figure 9A:
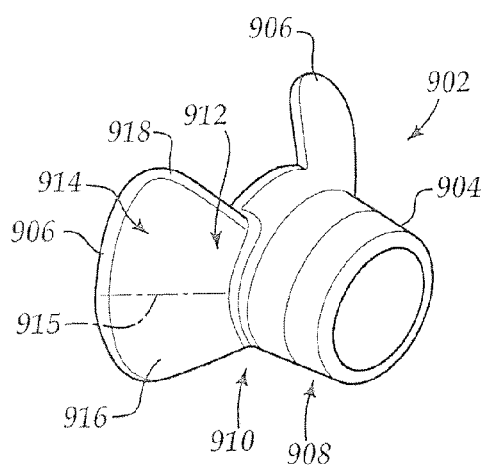
FIG. 9A is a schematic perspective view of a seventh embodiment of an anchoring unit for an electrical stimulation system, the anchoring unit including a body and anchoring members coupled to the body, the anchoring members increasing in width as the anchoring members extend away from the body, according to the invention.

In some embodiments, the anchoring members include tapered anchoring members. FIG. 9A is a schematic perspective view of a seventh embodiment of an anchoring unit 902. The anchoring unit 902 includes a body 904 and at least one anchoring member 906. The body 904 includes a first end 908 and a second end 910. The anchoring unit 902 includes a body 904 and at least one anchoring member 906.

The body 904 includes a first end 908 and a second end 910. The anchoring member 906 includes a proximal end 912, a distal end 914, a longitudinal axis 915, a first side 916, and a second side 918.

In at least some embodiments, the first side 916 and the second side 918 of the anchoring members 906 taper outward such that the distal end 914 is wider than the proximal end 912. In at least some embodiments, the anchoring members 906 extend from the second end 910 of the body 904 along a common transverse axis of the body 904. In at least some embodiments, two anchoring members 906 are disposed on opposing portions of the body 904 such that the two anchoring members 906 extend in opposite directions from the body 904. In at least some embodiments, the sum of the arc lengths of the distal ends 914 of the anchoring members 906 are no greater than the circumference of the body 904. In at least some embodiments, the widest portions of the anchoring members 906 have lengths that are at least as long as the diameter of the body 904.

Figure 9B:
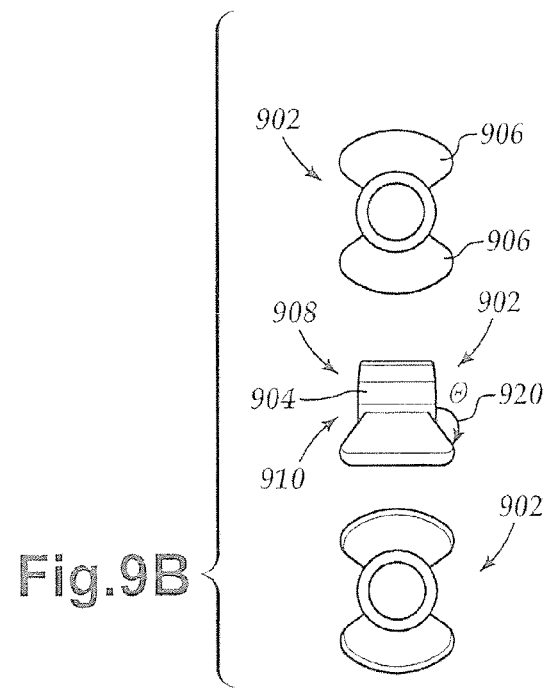
FIG. 9B is a schematic bottom view, side view, and top view of the anchoring unit shown in FIG. 9A, according to the invention.

FIG. 9B is a schematic bottom view, side view, and top view of the anchoring unit 902. In at least some embodiments, the anchoring members 906 are proximally biased. In other words, when the anchoring unit 902 is disposed on the lead body (106 in FIG. 1) so that the first end 908 is more distal on the lead body (106 in FIG. 1) than the second end 910, the anchoring members 906 form an angle with the longitudinal axis of the body 904 that is at least ninety degrees, as shown by angle Θ 920.

In some embodiments, the anchoring members include a secondary connecting member, such as a leaf spring, coupling the anchoring member to the body of the anchoring unit. FIG. 10A is a schematic perspective view of an eighth embodiment of an anchoring unit 1002. The anchoring unit 1002 includes a body 1004 and at least one anchoring member 1006. The body 1004 includes a first end 1008 and a second end 1010. The anchoring unit 1002 includes a body 1004 and at least one anchoring member 1006. The body 1004 includes a first end 1008 and a second end 1010. The anchoring member 1006 includes a proximal end 1012, a distal end 1014, a longitudinal axis 1015, a first side 1016, and a second side 1018.

In at least some embodiments, the first side 1016 and the second side 1018 of the anchoring member 1006 taper such that the proximal end 1012 of the anchoring member 1006 is wider than the distal end 1014. In at least some embodiments, the distal end 1014 of at least one of the anchoring members 1006 tapers to form a point. In a preferred embodiment, the point is rounded. In at least some embodiments, the first side 1016 and the second side 1018 of the anchoring member 1006 taper such that the distal end 1014 of the anchoring member 1006 is wider than the proximal end 1012. In at least some embodiments, the first side 1016 and the second side 1018 of the anchoring member 1006 are of approximately equal width.

In at least some embodiments, the anchoring unit 1002 further includes at least one secondary connecting member 1020 coupling the body 1004 to the distal end 1014 of one of the anchoring members 1006. In at least some embodiments, the at least one secondary connecting member 1020 is a leaf spring. In at least some embodiments, the secondary connecting member 1020 forms a solid surface between the body 1004 and the anchoring member 1006. In at least some other embodiments, the secondary connecting member 1020 forms at least one cutout 1022 between the body 1004, anchoring member 1006, and the secondary connecting member 1020. It may be a particular advantage of the anchoring unit 1002 that tissue ingrowth may occur in the cutouts 1022 to at least partially fill the cutouts 1022 with tissue to further increase the anchoring ability of the anchoring unit 1002.

In at least some embodiments, when the anchoring members 1006 are folded against the lead body (e.g., during insertion of the lead), the secondary connecting member 1020 stretches, thereby storing potential energy. The stored potential energy may facilitate anchoring of the anchoring member 1006 within patient tissue when the anchoring unit 1002 is released from the insertion needle and the stored potential energy is released.

FIG. 10B is a schematic bottom view, side view, and top view of the anchoring unit 1002. In at least some embodiments, the anchoring members 1006 extend from the second end 1010 of the body 1004 along a common transverse axis of the body 1004. In at least some embodiments, the anchoring members 1006 are proximally biased. In other words, when the anchoring unit 1002 is disposed on the lead body (106 in FIG. 1) so that the first end 1008 is more distal on the lead body (106 in FIG. 1) than the second end 1010, the anchoring members 1006 form an angle with the longitudinal axis of the body 1004 that is at least ninety degrees, as shown by angle Θ 1024.

In some embodiments, the one or more anchoring members are distally biased. FIG. 11A is a schematic perspective view of a ninth embodiment of an anchoring unit 1102. The anchoring unit 1102 includes a body 1104 and at least one anchoring member 1106. The body 1104 includes a first end 1108 and a second end 1110. The anchoring unit 1102 includes a body 1104 and at least one anchoring member 1106. The body 1104 includes a first end 1108 and a second end 1110. The anchoring member 1106 includes a proximal end 1112, a distal end 1114, a longitudinal axis 1115, a first side 1116, and a second side 1118.

In at least some embodiments, the first side 1116 and the second side 1118 of the anchoring member 1106 taper such that the proximal end 1112 of the anchoring member 1106 is wider than the distal end 1114. In at least some embodiments, the distal end 1114 of at least one of the anchoring members 1106 tapers to form a rounded point. In at least some embodiments, the first side 1116 and the second side 1118 of the anchoring member 1106 taper such that the distal end 1114 of the anchoring member 1106 is wider than the proximal end 1112. In at least some embodiments, the first side 1116 and the second side 1118 of the anchoring member 1106 are of approximately equal width.

In at least some embodiments, when the anchoring unit 1102 is separated from an insertion needle during insertion of the lead, the anchoring members 1106 are configured and arranged to extend within patient tissue. In some instances, the anchoring members 1106 are able to extend to distally-biased positions and in other instances they are not, depending on, for example, the amount of open space around the anchoring unit 1102 and the hardness of the surrounding tissue. For example, anchoring members 1106 may not be able to extend to distally-biased positions when positioned in a narrow space between hard tissues, such as bones or cartilage. When the anchoring members 1106 do extend to distally-biased positions, the anchoring members 1106 may resist withdrawal of the lead to which the anchoring unit 1102 is coupled. When patient tissue prevents the anchoring members 1106 from extending to distally-biased positions, the anchoring members 1106 fix the anchoring unit 1102 in position by the force of the anchoring members 1106 pressing against tissue in a manner similar to the proximally-biased anchoring members, discussed above. It may be an advantage of distally-biased anchoring members 1106 that, should an explant be necessary for the lead to which the anchoring unit 1102 is coupled, distally-biased anchoring members may be easier to remove from patient tissue than similarly-sized proximally-biased anchoring members.

FIG. 11B is a schematic bottom view, side view, and top view of the anchoring unit 1102. In at least some embodiments, the anchoring members 1106 extend from the second end 1110 of the body 1104 along a common transverse axis of the body 1104. In at least some embodiments, the anchoring members 1106 are distally biased. In other words, when the anchoring unit 1102 is disposed on the lead body (106 in FIG. 1) so that the first end 1108 is more distal on the lead body (106 in FIG. 1) than the second end 1110, the anchoring members 1106 form an angle with the longitudinal axis of the body 1104 that is no more than ninety degrees, as shown by angle Θ 1120.

Figure 12A:
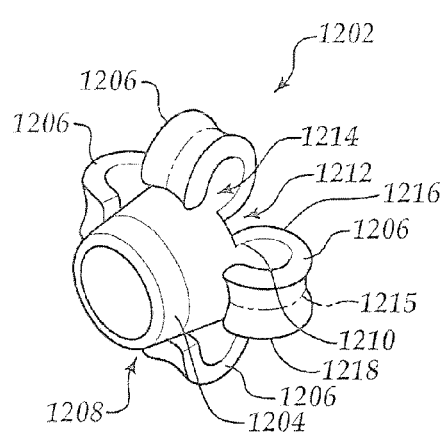
FIG. 12A is a schematic perspective view of a tenth embodiment of an anchoring unit for an electrical stimulation system, the anchoring unit including a body and curled anchoring members, each anchoring member curled to include a proximally-biased section and a distally-biased section, according to the invention.

In some embodiments, the one or more anchoring members are capable of curling such that a portion of at least one of the anchoring members is distally biased and a portion of the same anchoring member is proximally biased. FIG. 12A is a schematic perspective view of a tenth embodiment of an anchoring unit 1202. The anchoring unit 1202 includes a body 1204 and at least one anchoring member 1206. The body 1204 includes a first end 1208 and a second end 1210. The anchoring unit 1202 includes a body 1204 and at least one anchoring member 1206. The body 1204 includes a first end 1208 and a second end 1210. The anchoring member 1206 includes a proximal end 1212, a distal end 1214, a curled longitudinal axis 1215, a first side 1216, and a second side 1218. In at least some embodiments, the anchoring members 1206 have an arc-shaped transverse profile.

In at least some embodiments, the first side 1216 and the second side 1218 of the anchoring member 1206 taper such that the proximal end 1212 of the anchoring member 1206 is wider than the distal end 1214. In at least some embodiments, the distal end 1214 of at least one of the anchoring members 1206 tapers to form a rounded point. In at least some embodiments, the first side 1216 and the second side 1218 of the anchoring member 1206 taper such that the distal end 1214 of the anchoring member 1206 is wider than the proximal end 1212. In at least some embodiments, the first side 1216 and the second side 1218 of the anchoring member 1206 are of approximately equal width.

In at least some embodiments, the anchoring members 1206 are configured and arranged to lie flat during insertion of the lead and curl upon separation from an insertion needle. In at least some embodiments, the anchoring members 1206 have an arc-shaped transverse profile that facilitates the anchoring members 1206 lying flat against the lead. In at least some embodiments, when the anchoring unit 1202 is separated from an insertion needle during insertion of the lead, the anchoring members 1206 are configured and arranged to curl up such that the anchoring members 1206 extend within patient tissue. The anchoring members may include a metal, such as nitinol, or a polymer that is configured and arranged to curl when unconstrained. In some instances, the anchoring members 1206 are able to extend to distally-biased positions and in other instances they are not, depending on, for example, the amount of open space around the anchoring unit 1202 and the hardness of the surrounding tissue. For example, anchoring members 1206 may not be able to extend to distally-biased positions when positioned in a narrow space between hard tissues, such as bones or cartilage. When the anchoring members 1206 do extend to distally-biased positions, the anchoring members 1206 may resist withdrawal of the lead to which the anchoring unit 1202 is coupled. When patient tissue prevents the anchoring members 1206 from extending to distally-biased positions, the anchoring members 1206 fix the anchoring unit 1202 in position by the force of the anchoring members 1206 pressing against tissue in a manner similar to the proximally-biased anchoring members, discussed above.

Figure 12B:
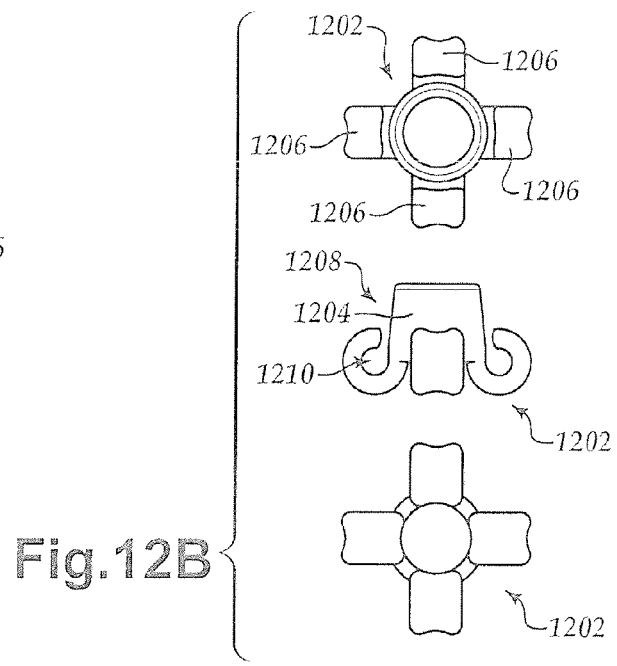
FIG. 12B is a schematic bottom view, side view, and top view of the anchoring unit shown in FIG. 12A, according to the invention.

FIG. 12B is a schematic bottom view, side view, and top view of the anchoring unit 1202. In at least some embodiments, the anchoring members 1206 extend from the second end 1210 of the body 1204 along a common transverse axis of the body 1104. In at least some embodiments, at least one of the anchoring members 1206 is configured and arranged to curl up such that a portion of that anchoring member is proximally biased and a portion of that anchoring member is distally biased.

Figure 13A:
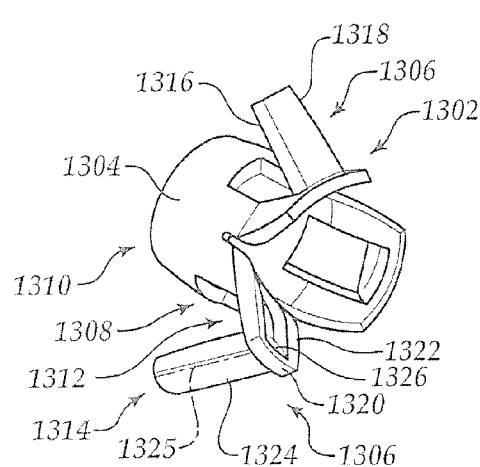
FIG. 13A is a schematic perspective view of an eleventh embodiment of an anchoring unit for an electrical stimulation system, the anchoring unit including a body and articulated anchoring members, each anchoring member including a proximally-biased section and a distally-biased section, according to the invention.

In some embodiments, the one or more anchoring members extend from the body at the second end of the body, which, as discussed above, is the end of the body that is positioned more proximally than the first end when the anchoring unit is disposed on the lead body (106 in FIG. 1). In some embodiments, the one or more anchoring members are articulated. FIG. 13A is a schematic perspective view of an eleventh embodiment of an anchoring unit 1302. The anchoring unit 1302 includes a body 1304 and at least one anchoring member 1306. The body 1304 includes a first end 1308 and a second end 1310. The anchoring unit 1302 includes a body 1304 and at least one anchoring member 1306. The body 1304 includes a first end 1308 and a second end 1310. The anchoring member 1306 includes a proximal end 1312, a distal end 1314, a longitudinal axis 1315, a first side 1316, and a second side 1318.

At least one of the anchoring members 1306 includes at least one articulation 1320 dividing the anchoring member 1306 into a plurality of sections. In at least one embodiment, the articulation 1320 divides the anchoring member 1306 into a proximal section 1322 and a distal section 1324. In at least some embodiments, the proximal section 1322 includes at least one cutout 1326. It may be a particular advantage of the anchoring unit 1302 that tissue may at least partially fill the cutouts 1326 defined in the proximal section 1322 of the anchoring member 1306 to further increase the anchoring ability of the anchoring unit 1302. In at least some embodiments, the distal sections 1324 of the anchoring members 1306 are configured and arranged to fold into the cutouts 1326 defined in the proximal sections 1322 of the anchoring members 1306 (e.g., during insertion of the lead).

In at least some embodiments, the proximal section 1322 of at least one of the anchoring members 1306 is wider than the distal section 1324 of the anchoring member 1306. In at least some embodiments, the distal end 1314 of at least one of the anchoring members 1306 tapers to form a point. In a preferred embodiment, the point is rounded. In at least some embodiments, the proximal section 1314 of at least one of the anchoring members 1306 is narrower than the distal section 1316 of the anchoring member 1306. In at least some embodiments, the proximal section 1314 of at least one of the anchoring members 1306 is of approximately equal width to the distal section 1316 of the anchoring member 1306.

Figure 13B:
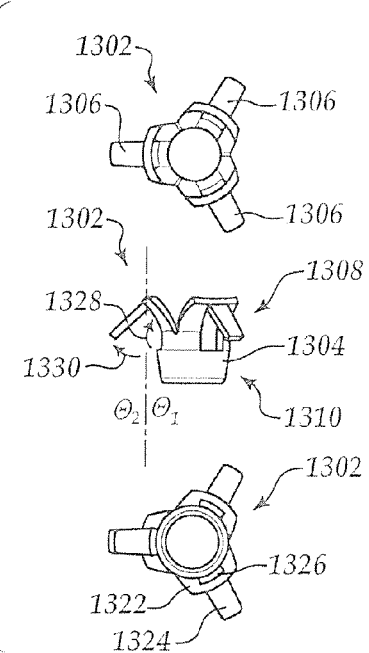
FIG. 13B is a schematic bottom view, side view, and top view of the anchoring unit shown in FIG. 13A, according to the invention.

FIG. 13B is a schematic bottom view, side view, and top view of the anchoring unit 1302. In at least some embodiments, the proximal sections 1322 of the anchoring members 1306 are proximally biased and the distal sections 1324 of the anchoring members 1306 are distally biased. In other words, when the anchoring unit 1302 is disposed on the lead body (106 in FIG. 1) so that the first end 1308 is more distal on the lead body (106 in FIG. 1) than the second end 1310, the proximal sections 1314 of the anchoring members 1306 form an angle with the longitudinal axis of the body 1304 that are greater than ninety degrees, as shown by angle $\Theta_1$ 1328 and the distal sections 1324 of the anchoring members 1306 form an angle with the longitudinal axis of the body 1304 that are no greater than ninety degrees, as shown by angle $\Theta_2$ 13.

Unless indicated otherwise, the following characteristics of the anchoring units, or its components, or the corresponding lead apply equally to each of the embodiments shown in FIG. 4C-13B. In at least some embodiments, the body is substantially tubular-shaped with a diameter and a longitudinal axis that is perpendicular to a transverse axis of the body. In at least some embodiments, the diameter of the body of the anchoring unit is approximately equal to the diameter of the lead body (106 in FIG. 1). In at least some embodiments, the longitudinal axis of at least one of the anchoring member is at least half the length of the diameter of the body. In at least some embodiments, the longitudinal axis of at least one of the anchoring members is no less than the length of the diameter of the body. In at least some embodiments, the body is cuff-shaped. In at least some embodiments, the anchoring members extend from the second end of the body (except for anchoring member 1306). In at least some embodiments, the anchoring members are proximally biased (except for anchoring members 1106, 1206, and 1306).

In at least some embodiments, the longitudinal axis of the anchoring members extend to a distal end. In some embodiments, the anchoring members may have a distal end that is of approximately equal width as the proximal end (except for anchoring members 406, 606, 806, 906, and 1306). In at least some embodiments, the distal end may be narrower than the proximal end (except for anchoring members 606, 806, and 906). In at least some embodiments, the distal end may be wider than the proximal end (except for anchoring members 406, 806, and 1306).

In at least some embodiments, at least one of the anchoring members is formed integrally with the body. In at least some embodiments, at least one of the anchoring units is formed separately from the body and is coupleable to the body. In at least some embodiments, the anchoring members may include one or more features (e.g., barbs, ridges, fissures, knobs, grooves, and the like) coupled to, or formed with, the anchoring members for facilitating the anchoring ability of the anchoring unit when the anchoring unit is implanted in a patient.

Any suitable number of anchoring members may be coupled to, or formed with, the body including, for example, one, two, three, four, five, six, seven, eight, nine, ten or more anchoring members. As will be recognized, other numbers of anchoring members may also be coupled to, or formed with, the body.

In at least some embodiments, the anchoring unit may induce the formation of tissue ingrowth around at least a portion of the anchoring unit within the usable lifespan of the anchoring unit. In at least some embodiments, the usable lifespan may vary depending on the indication and location of the lead to which the anchoring unit is coupled while implanted in a patient. It may be an advantage to have tissue ingrowth around at least a portion of the anchoring unit because the tissue ingrowth may further increase the anchoring ability of the anchoring unit when the anchoring unit is implanted in a patient. In the embodiments shown in FIGS. 6A-7B and 10A-10B, additional tissue ingrowth may occur between open spaces between components of the anchoring unit (e.g., slits 620, open space 722, and cutout 1022).

In at least some embodiments, the anchoring members are flexible. In at least some embodiments, when the anchoring unit is coupled to a lead body (106 in FIG. 1), the anchoring members are configured and arranged to fold flat against the lead body (106 in FIG. 1) during insertion of the lead. For example, when, in at least some embodiments, a lead is inserted into a conventionally-sized insertion needle during implantation of the lead, the anchoring members fold against the lead body (106 in FIG. 1) without interfering with one another so that the lead is able to fit into a cannula of the conventionally-sized insertion needle. In at least some embodiments, at least one of the anchoring members is contoured to facilitate the folding of the anchoring members. In the embodiments shown in FIGS. 8A-8B, at least a portion of at least one of the anchoring members 806 may need to deform onto itself while in a folded position.

Figure 14:
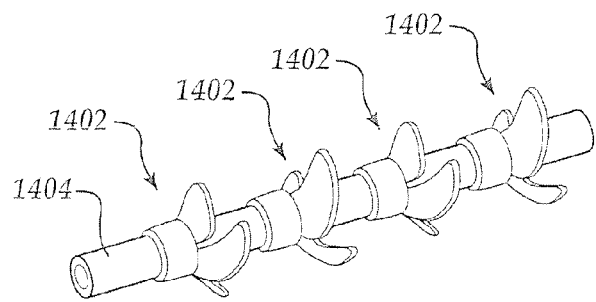
FIG. 14 is a schematic perspective view of one embodiment of a portion of a lead body of an electrical stimulation system on which four similarly-shaped anchoring units are disposed, according to the invention.

In at least some embodiments, one or more anchoring units may be disposed on the lead body (106 of FIG. 1). In at least some embodiments, multiple anchoring units may be employed which have similarly-shaped anchoring members. FIG. 14 is a schematic perspective view of one embodiment of four anchoring units 1402 disposed on a portion of a lead body 1404. In at least some embodiments, the anchoring units 1402 are evenly-spaced from one another. In at least some embodiments, at least some of the anchoring units 1402 are irregularly spaced from one another. In at least some embodiments, at least one of the anchoring units 1402 may be of a different size from the remaining anchoring units 1402. In at least some embodiments, the anchoring members of different anchoring units are aligned with respect to one another along the longitudinal axis of the lead body. In at least some other embodiments, the anchoring members of different anchoring units are staggered, unaligned, or randomly positioned with respect to other anchoring members along the lead body.

Figure 15:
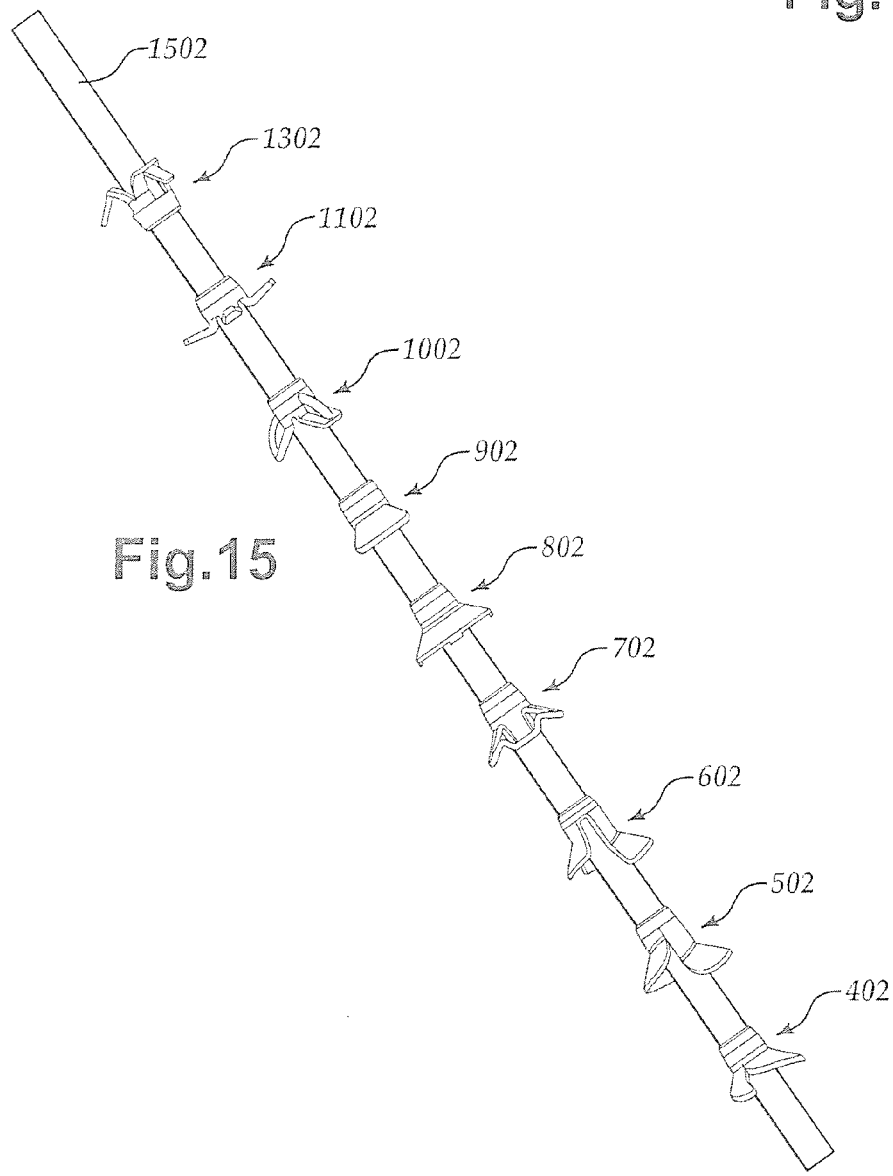
FIG. 15 is a schematic perspective view of one embodiment of a portion of a lead body of an electrical stimulation system on which nine differently-shaped anchoring units are disposed, according to the invention.

In at least some embodiments, multiple anchoring units may be disposed on a portion of the lead body, at least some of which have differently-shaped anchoring members. FIG. 15 is a schematic side view of one embodiment of nine different anchoring units 402, 502, 602, 702, 802, 902, 1002, 1102, and 1302 disposed on a portion of the lead body 1502. In at least some embodiments, the anchoring units 402, 502, 602, 702, 802, 902, 1002, 1102, and 1302 are evenly-spaced from one another. In at least some embodiments, at least some of the anchoring units 402, 502, 602, 702, 802, 902, 1002, 1102, and 1302 are irregularly spaced from one another. In at least some embodiments, at least one of the anchoring units 402, 502, 602, 702, 802, 902, 1002, 1102, and 1302 may be of a different size from the remaining anchoring units 402, 502, 602, 702, 802, 902, 1002, 1102, and 1302.

Figure 16:
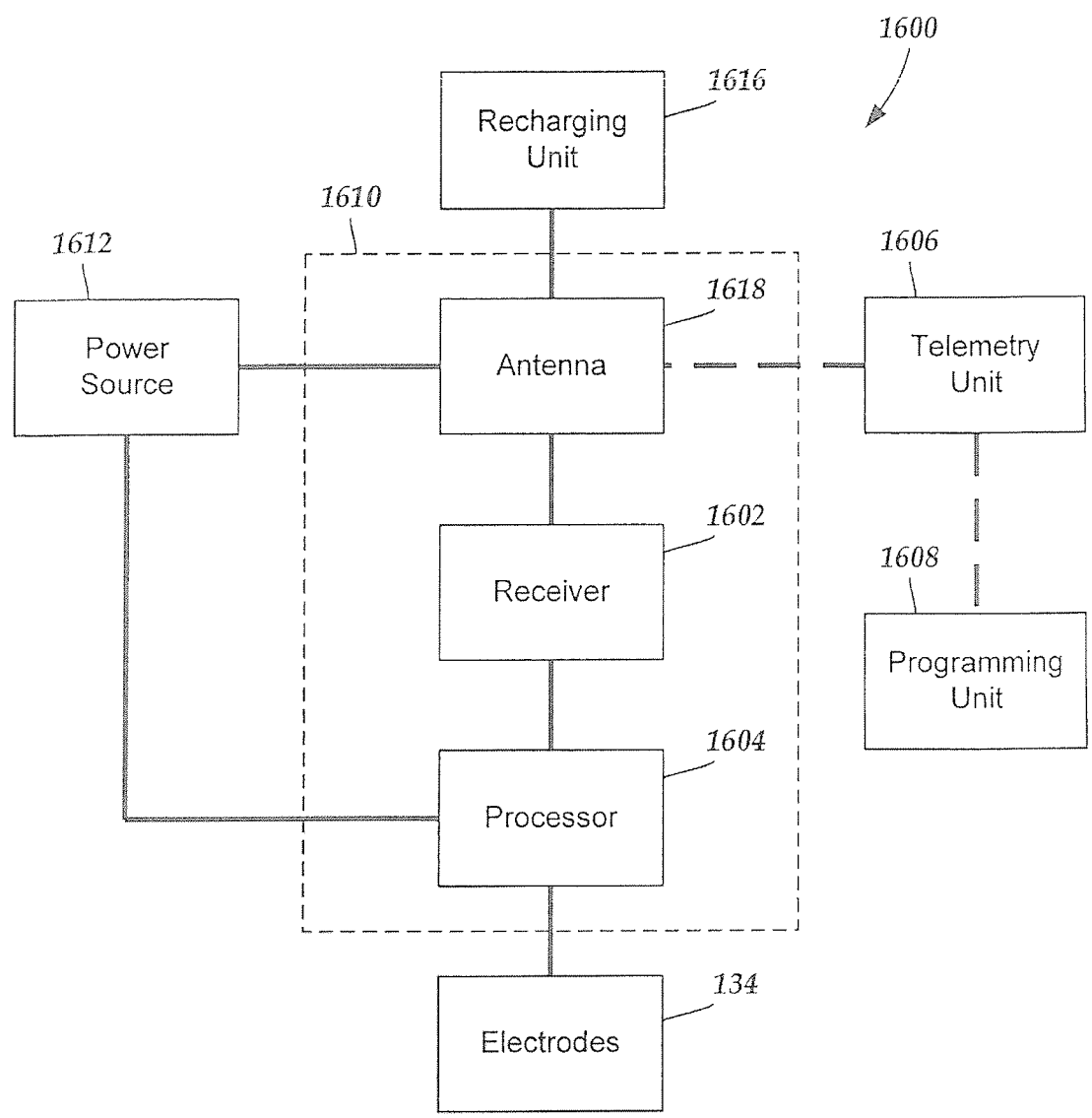
FIG. 16 is a schematic overview of one embodiment of components of a stimulation system, including an electronic subassembly disposed within a control module, according to the invention.

FIG. 16 is a schematic overview of one embodiment of components of an electrical stimulation system 1600 including an electronic subassembly 1610 disposed within a control module. It will be understood that the electrical stimulation system can include more, fewer, or different components and can have a variety of different configurations including those configurations disclosed in the stimulator references cited herein.

Some of the components (for example, power source 1612, antenna 1618, receiver 1602, and processor 1604) of the electrical stimulation system can be positioned on one or more circuit boards or similar carriers within a sealed housing of an implantable pulse generator, if desired. Any power source 1612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1618 or a secondary antenna. The external power source can be in a device that is mounted on the skin of the user or in a unit that is provided near the user on a permanent or periodic basis.

If the power source 1612 is a rechargeable battery, the battery may be recharged using the optional antenna 1618, if desired. Power can be provided to the battery for recharging by inductively coupling the battery through the antenna to a recharging unit 1616 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1604 is generally included to control the timing and electrical characteristics of the electrical stimulation system. For example, the processor 1604 can, if desired, control one or more of the timing, frequency, strength, duration, and waveform of the pulses. In addition, the processor 1604 can select which electrodes can be used to provide stimulation, if desired. In some embodiments, the processor 1604 may select which electrode(s) are cathodes and which electrode(s) are anodes. In some embodiments, the processor 1604 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1608 that, for example, allows modification of pulse characteristics. In the illustrated embodiment, the processor 1604 is coupled to a receiver 1602 which, in turn, is coupled to the optional antenna 1618. This allows the processor 1604 to receive instructions from an external source to, for example, direct the pulse characteristics and the selection of electrodes, if desired.

In one embodiment, the antenna 1618 is capable of receiving signals (e.g., RF signals) from an external telemetry unit 1606 which is programmed by a programming unit 1608. The programming unit 1608 can be external to, or part of, the telemetry unit 1606. The telemetry unit 1606 can be a device that is worn on the skin of the user or can be carried by the user and can have a form similar to a pager, cellular phone, or remote control, if desired. As another alternative, the telemetry unit 1606 may not be worn or carried by the user but may only be available at a home station or at a clinician's office. The programming unit 1608 can be any unit that can provide information to the telemetry unit 1606 for transmission to the electrical stimulation system 1600. The programming unit 1608 can be part of the telemetry unit 1606 or can provide signals or information to the telemetry unit 1606 via a wireless or wired connection. One example of a suitable programming unit is a computer operated by the user or clinician to send signals to the telemetry unit 1606.

The signals sent to the processor 1604 via the antenna 1618 and receiver 1602 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1600 to cease operation, to start operation, to start charging the battery, or to stop charging the battery. In other embodiments, the stimulation system does not include an antenna 1618 or receiver 1602 and the processor 1604 operates as programmed.

Optionally, the electrical stimulation system 1600 may include a transmitter (not shown) coupled to the processor 1604 and the antenna 1618 for transmitting signals back to the telemetry unit 1606 or another unit capable of receiving the signals. For example, the electrical stimulation system 1600 may transmit signals indicating whether the electrical stimulation system 1600 is operating properly or not or indicating when the battery needs to be charged or the level of charge remaining in the battery. The processor 1604 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead, comprising:
   a lead body having a proximal end portion, a distal end portion, and an outer surface;
   a plurality of electrodes disposed along the distal end portion of the lead body;
   a plurality of terminals disposed along the proximal end portion of the lead body;
   a plurality of conductors electrically coupling the electrodes to the terminals; and
   at least one anchoring unit disposed along the lead body, each of the at least one anchoring unit comprising
      a body configured and arranged for positioning along a portion of the outer surface of the lead body, the body having a first end and a second end and a longitudinal axis extending therebetween, the first end being configured and arranged for placement on the lead body so that the first end is positioned more distally on the lead than the second end;
      a plurality of anchoring members extending from the body of the anchoring unit and away from the lead body, each anchoring member having a proximal end and a distal end, the proximal end of each anchoring member coupled to the body and the distal end of each anchoring member configured and arranged for extending into tissue of a patient to anchor the anchoring unit to the tissue of the patient upon implantation of the implantable lead into the patient; and
      a conical sheath completely covering each of the plurality of anchoring member;
         wherein each of the plurality of anchoring members and the sheath is configured and arranged to fold flat when the lead is inserted into a cannula.

2. The lead of claim 1, wherein the sheath comprises continuous, conical sheet stretching between and over the plurality of anchoring members.

3. The lead of claim 1, wherein at least one of the plurality of anchoring members extends from the second end of the body.

4. The lead of claim 1, wherein at least one of the plurality of anchoring members extends from the second end of the body such that the at least one anchoring member forms an angle with the longitudinal axis of the body that is at least ninety degrees.

5. The lead of claim 1, wherein at least one of the plurality of anchoring members extends from the first end of the body.

6. The lead of claim 1, wherein the distal end and the proximal end of at least one of the plurality of anchoring members have equal widths.

7. The lead of claim 1, wherein tissue ingrowth forms over at least a portion of the at least one anchoring unit during a useful lifespan of the at least one anchoring unit.

8. An electrical stimulating system comprising:
   the lead of claim 1;
   a control module configured and arranged to electrically couple to the proximal end portion of the lead body, the control module comprising
      a housing, and
      an electronic subassembly disposed in the housing; and
   a connector for receiving the lead, the connector comprising
      a connector housing defining a port at the distal end of the connector, the port configured and arranged for receiving the proximal end portion of the lead body, and
      a plurality of connector contacts disposed in the connector housing, the connector contacts configured and arranged to couple to at least one of the plurality of terminals disposed on the proximal end portion of the lead body.

9. The electrical stimulating system of claim 8, wherein the connector is disposed on the control module.

10. The electrical stimulating system of claim 8, further comprising a lead extension, wherein the connector is disposed on a distal end of the lead extension.

11. The electrical stimulating system of claim 10, wherein the control module further comprises a second connector, wherein the lead extension has a proximal end that couples with the second connector disposed on the control module.

12. A method of stimulating patient tissue comprising:
   providing the lead of claim 1;
   inserting the lead into a patient such that the electrodes of the lead are in proximity to the patient tissue to be stimulated;
   coupling the lead to a control module;
   generating electrical signals using the control module; and
   propagating the generated electrical signals to the electrodes of the lead.

13. An implantable lead, comprising:
   a lead body having a proximal end portion, a distal end portion, and an outer surface;
   a plurality of electrodes disposed along the distal end portion of the lead body;
   a plurality of terminals disposed along the proximal end portion of the lead body;
   a plurality of conductors electrically coupling the electrodes to the terminals; and
   at least one anchoring unit, each of the at least one anchoring unit comprising
      a body configured and arranged for positioning along a portion of the outer surface of the lead body, the body having a first end and a second end and a longitudinal axis extending therebetween, the first end being configured and arranged for placement on the lead body so that the first end is positioned more distally on the lead than the second end; and a sheath disposed concentrically around the lead body and extending outwardly from the body of the anchoring unit and away from the lead body, the sheath comprising a continuous, conical sheet and having a proximal unit and a distal end, the proximal end of the sheath coupled to the body of the anchoring unit and the distal end of the sheath configured and arranged for extending into tissue of a patient to anchor the anchoring unit to the tissue of the patient upon implantation of the implantable lead into the patient;

wherein each of the anchoring units is configured and arranged to fold flat against the outer surface of the lead body when the lead is inserted into a cannula.

14. The lead of claim 13, wherein the distal end of the sheath has a first inner diameter and the proximal end of the sheath has a second inner diameter, wherein the first inner diameter is greater than the second inner diameter.

15. The lead of claim 13, wherein the sheath is configured and arranged to fold when the lead is inserted into a cannula.

16. The lead of claim 13, wherein the lead is configured and arranged to permit ingrowth of tissue between the sheath and the lead body.

17. An electrical stimulating system comprising:
the lead of claim 13;
a control module configured and arranged to electrically couple to the proximal end portion of the lead body, the control module comprising
a housing, and
an electronic subassembly disposed in the housing; and
a connector for receiving the lead of the lead assembly, the connector comprising
a connector housing defining a port at the distal end of the connector, the port configured and arranged for receiving the proximal end portion of the lead body, and
a plurality of connector contacts disposed in the connector housing, the connector contacts configured and arranged to couple to at least one of the plurality of terminals disposed on the proximal end portion of the lead body.

18. A method of stimulating patient tissue comprising:
providing the lead of claim 13
inserting the lead into a patient such that the electrodes of the lead are in proximity to the patient tissue to be stimulated;
coupling the lead to a control module;
generating electrical signals using the control module; and
propagating the generated electrical signals to the electrodes of the lead.

* * * * *